United States Patent [19]

Schulte-Elte et al.

[11] 4,453,000
[45] Jun. 5, 1984

[54] TRICYCLIC COMPOUNDS AND USE THEREOF AS PERFUME INGREDIENTS

[75] Inventors: Karl-Heinrich Schulte-Elte, Onex; Hervé Pamingle, Geneva, both of Switzerland

[73] Assignee: Firmenich, S.A., Geneva, Switzerland

[21] Appl. No.: 496,002

[22] Filed: May 19, 1983

Related U.S. Application Data

[63] Continuation-in-part of Ser. No. 265,998, May 21, 1981.

[30] Foreign Application Priority Data

May 27, 1981 [CH] Switzerland .......................... 4088/80

[51] Int. Cl.³ .................... C07C 67/02; C07C 35/22; C11B 9/00; A61K 7/46; A61K 7/06
[52] U.S. Cl. ................................... 560/256; 568/817; 252/522 R; 252/522 A; 424/70
[58] Field of Search .................. 560/256; 568/817; 252/522 R, 522 A; 424/70

[56] References Cited

U.S. PATENT DOCUMENTS

| 3,953,534 | 4/1976 | Sundt | 560/256 |
| 4,318,863 | 3/1982 | Sprecker et al. | 560/256 |
| 4,386,023 | 5/1983 | Sprecker et al. | 252/522 R |

FOREIGN PATENT DOCUMENTS

2642519  3/1978  Fed. Rep. of Germany ...... 560/256

OTHER PUBLICATIONS

Patterson et al., The Ring Index, American Chemical Society, Second Edition, p. 293.
Chemical Abstracts, Ninth Collective Index, Chemical Substances, p. 23178CS, 1978.

*Primary Examiner*—Glennon H. Hollrah
*Assistant Examiner*—Bruce D. Gray
*Attorney, Agent, or Firm*—Scully, Scott, Murphy & Presser

[57] ABSTRACT

New tricyclic compounds and use thereof as perfume ingredients. Perfume compositions and perfumed articles containing same.

7 Claims, No Drawings

TRICYCLIC COMPOUNDS AND USE THEREOF AS PERFUME INGREDIENTS

RELATED U.S. APPLICATION DATA

Continuation-in-part of Ser. No. 265,998, filed May 21, 1981.

BRIEF SUMMARY OF THE INVENTION

The invention relates to novel tricyclic compounds of formula

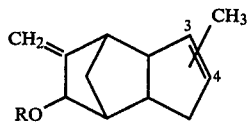

possessing a methyl radical at position 3 or 4 and wherein symbol R represents a lower acyl radical namely to those compounds of formula (I) represented by one of the following stereoisomeric forms:

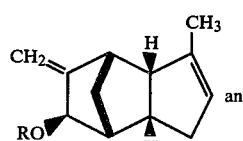 and 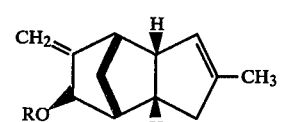

(Ia)          (Ib)

wherein symbol R is defined as for formula (I).

BACKGROUND OF THE INVENTION

U.S. Pat. No. 4,318,863, issued on Mar. 9, 1982 and assigned to International Flavors & Fragrances, describes substituted tricyclodecane derivatives having the generic formula

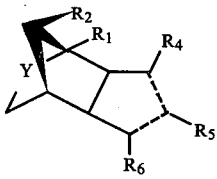

wherein Y is a moiety having a structure selected from the group consisting of:

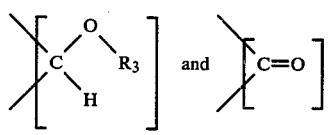

wherein one of the dashed lines represents a carbon-carbon single bond and the other of the dashed lines represents a carbon-carbon double bond; wherein $R_1$ and $R_2$ represent hydrogen or methyl with the proviso that one of $R_1$ and $R_2$ is hydrogen and the other of $R_1$ and $R_2$ is methyl; wherein $R_3$ is hydrogen, $C_1$-$C_3$ acyl, $C_3$ or $C_4$ alkyl or $C_3$ or $C_4$ alkenyl; wherein $R_4$, $R_5$ and $R_6$ represent hydrogen or methyl with the additional proviso that one of $R_4$, $R_5$ and $R_6$ is methyl and the other two of $R_4$, $R_5$ and $R_6$ is hydrogen. Also described are processes for using the above defined compounds for their organoleptic properties.

Among the great variety of tricyclodecane derivatives depicted by the above given formula, the following are worth mentioning:

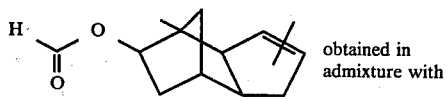 obtained in admixture with

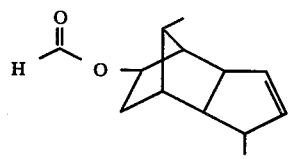

and

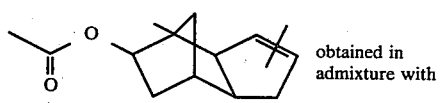 obtained in admixture with

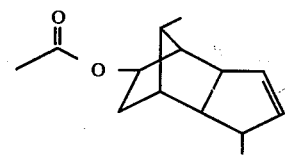

(see Examples I and II of the cited U.S. patent).

Though these compounds of the prior art bear a certain similarity, from the structure point of view, with compounds (I) of the instant invention, they present quite distinct organoleptic properties therefrom.

While the first of the described mixtures possess a fragrance profile characterized by a strong maple aroma with pumpkin-like and slightly spicy undertones, the second one shows a fruity, anisic aroma with a raspberry undertone which on dryout becomes fruity and berry-like (see cited U.S. Pat. No. 4,318,863, columns 16 and 17).

We have discovered that the compounds of the instant invention develop a warm aromatic fragrance with a top note reminiscent of certain spicy ingredients like basil or sage. These fragrance characters are to be found in tagete flowers or marigold. They develop moreover an undertone of earthy and woody type which tends to become dominant in the dry-out.

In actual experience, one could not expect to replace the instant compounds of formula (I) with the prior art ones in a given perfume composition. The distinctiveness of their respective odor properties is such that their use satisfies different needs and achieves dissimilar results.

The invention also relates to a method for modifying, enhancing or improving the odour properties of perfume compositions or perfumed articles, which comprises adding thereto a small but olfactively effective amount of a compound represented by one of the formulae given hereinabove.

The invention finally relates to a perfume composition or a perfumed article which comprises, as olfactively active ingredient, a compound represented by one of the formulae given hereinabove.

In the formulae given hereinabove, the term "lower acyl" is deemed to define an acyl radical containing from 1 to 4 carbon atoms, viz. formyl, acetyl, propionyl, butyryl and isobutyryl.

PREFERRED EMBODIMENTS OF THE INVENTION

In view of their original odour properties, compounds of formula (I) are particularly useful for the preparation of perfumes, perfume compositions or perfume bases of various types or for the manufacture of perfumed articles such as soaps, detergents, household materials or cosmetic preparations.

The proportions to be used in order to achieve odour effects such as those described hereinabove may vary within a wide range. Interesting effects may already be achieved by using proportions comprised between about 0.1 and 0.5% by weight of the weight of the article to be perfumed. Higher proportions, of the order of 10, 20% or more, can also be used especially for the preparation of perfume compositions or perfume bases.

Such concentrations, however, must not be interpreted in a restricted way, as they may obviously depend on the nature of the coingredients of a given perfume composition or the nature of the article to be perfumed.

The compounds of formula (I), which are new chemicals, can be prepared in accordance with conventional techniques from the dimers of methyl-cyclopentadiene as illustrated by the following reaction scheme:

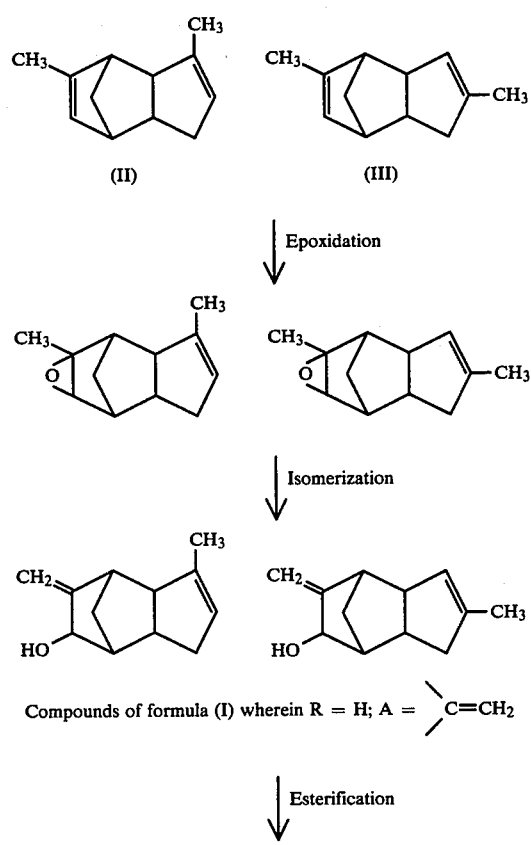

-continued

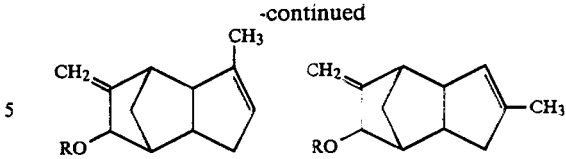

The above synthetic process can be carried out by using either one of the pure dimers of formula (II) or (III) or any mixture thereof. For economical and practical reasons, however, it is preferred to use a commercial mixture containing about 45% of dimer (II) and about 30% of dimer (III) as available, for example, from Aldrich Chemical Co. Inc., Milwaukee, Wis. (USA). In such a case, the final products can be isolated by means of the usual techniques, e.g. chromatography or fractional distillation. Another type of separation can be effected on the isomeric mixture of epoxides as obtained from the first reaction step, the subsequent isomerization and esterification being then applied to each one of the pure isomeric epoxides. The above separation method will be illustrated in one of the examples given hereinafter.

Compounds of formula (I), as directly obtained from the above synthetic process, may exist under different stereoisomeric forms depending on the nature of the starting material used. By using commercially available isomeric mixture of methylcyclopentadiene dimers (origin: Aldrich Chemical Co. Inc.), the following stereoisomers were obtained:

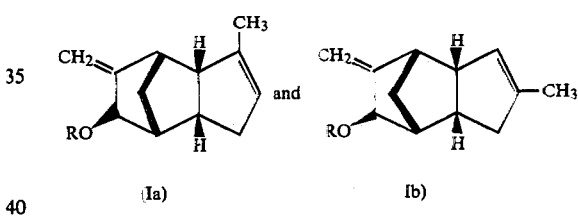

(Ia)    (Ib)

It has been observed, in most cases, that stereoisomers (Ia) and (Ib) possess similar odour properties and that mixtures of same, as directly synthetically obtained, may advantageously be used in accordance with the invention.

The following examples are deemed to illustrate the invention in a more detailed manner (temperatures given in degrees centigrade).

EXAMPLE 1

Preparation of the esters of 3-methyl-9-methylene-endo-tricyclo[5.2.1.0$^{2,6}$]dec-3-ene-8(exo)-ol(IA) and 4-methyl-9-methylene-endo-tricyclo[5.2.1.0$^{2,6}$]dec-3-ene-8-(exo)-ol (IB)

(a) epoxidation of methyl-cyclopentadiene dimers 1.2 moles (200 g) of a commercial mixture of 3,9-dimethyl-tricyclo[5.2.1.0$^{2,6}$] deca-3,8-diene and 4,9-dimethyl-tricyclo[5.2.1.0$^{2,6}$] deca-3,8-diene (origin: Aldrich Chemical Co. Inc.) were added to 500 ml of methylene chloride and 1.5 moles of anhydrous sodium acetate. To the above mixture, cooled at 0°, there were added dropwise a mixture of 190 g of 40% peracetic acid and 10 g of anhydrous sodium acetate: reaction temperature ca. 5°. The reaction mixture was further stirred at 5° for 1 hour, then kept overnight at room temperature and finally diluted with 1000 ml of ice/water. After separation of the organic layer, neutralization with aqueous NaHCO₃, drying and evaporation, the desired epoxides were isolated by means of a distillation (pressure 12-20 Torr) on a spinning band column.

(ai) the epoxidation of pure 3,9-dimethyl-tricyclo[5.2.1.0²,⁶]deca-3,8-diene according to the above method yielded 188 g of a mixture containing the two epoxides defined hereinbelow

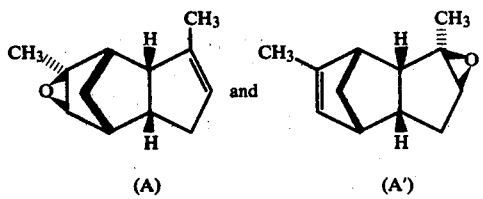

in the proportions of 56 and 19%, respectively. Each of epoxides A and A' were isolated by distillation on a spinning band column (length: 80 cm).

(A) b.p. 112°/16 Torr-colourless liquid with a minty and camphor-like odour;

IR (liquid film, NaCl): 3040, 1645, 800 cm⁻¹;

NMR (360 MHz, CDCl₃): 0.8 (1H, d); 1.32 (3H,s); 1.58 (1H, dxt); 1.74 (3H,d); 2.18 (1H, m); 2.2 (1H, m); 2.38 (1H, m); 2.45 (1H, m); 2.73 (1H, m); 2.91 (1H, d); 3.06 (1H, s); 5.27 (1H, m) δppm;

MS: M⁺=176(25); m/e: 161(5), 143(10), 128(6), 115(6), 105(12), 96(78), 81(100), 65(8), 53(10), 35(15), 27(11).

(A') b.p. 104°/16 Torr-colourless liquid with minty and camphor-like odour; IR (liquid film, NaCl): 3040, 1640, 920, 830 cm⁻¹;

NMR (60 MHz, CDCl₃): 1.42 (3H, s); 1.88 (3H, d); 3.22 (1H, d); 5.73 (1H, m)δppm;

MS: M⁺=176(2); m/e: 158(3), 143(1), 133(1), 119(2), 109(2), 96(8), 81(15), 80(100), 79(30), 67(4), 53(4), 39(7), 27(4).

(aii) the epoxidation of pure 4,9-dimethyl-tricyclo[5.2.1.0²,⁶]deca-3,8-diene in accordance with the above method yielded 182 g of a mixture containing the two epoxides defined hereinbelow.

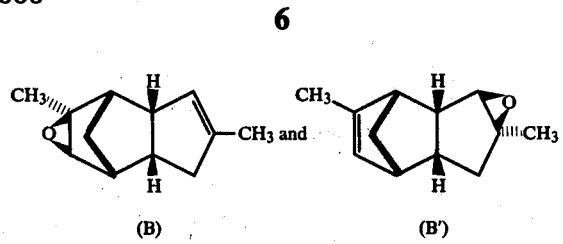

in the proportions of 40 and 26%, respectively. Epoxides B and B' were separated as indicated for A and A'.

(B) b.p. 106°/16 Torr-colourless oil with a camphor-like odour;

IR (liquid film, NaCl): 3050, 1680, 815 cm⁻¹;

NMR (360 MHz, CDCl₃): 0.78 (1H, d); 1.31 (3H, s); 1.5 (1H, dxt); 1.67 (3H, d); 2.07 (1H, d); 2.17 (1H, dxd); 2.48 (1H, m); 3.12 (2H, m); 5.28 (1H, m)δppm;

MS: M⁺=176(18); m/e: 161(8), 143(13), 133(16), 119(8), 105(17), 96(100), 95(92), 80(72), 79(90), 65(9), 53(13), 41(20), 27(15).

(B') b.p. 102°/16 Torr-colourless oil with a camphor-like odour;

IR (liquid film, NaCl): 3060, 1640, 812, 800 cm⁻¹;

NMR (60 MHz, CDCl₃): 1.26 (3H, s); 1.77 (3H, d); 3.02 (1H, s); 5.7 (1H, m)δppm;

MS: M⁺=176(11); m/e: 158(2), 147(3), 133(8), 119(4), 105(6), 95(25), 81(25), 80(100), 79(29), 67(4), 53(4), 41(11), 27(6).

(aiii) the epoxidation of the commercial mixture of methyl-cyclopentadiene dimers (see letter a above) yielded 180 g of a mixture containing
14 g of epoxide B'
16 g of epoxide A'
28 g of epoxide B and
49 g of epoxide A.

(b) isomerization of epoxides 1 part by weight of the selected epoxide (single compound or mixture of same; see above) in admixture with 0.15 part of freshly distilled aluminum isopropylate and 5 to 8 parts of toluene were heated to reflux for 1 hour under nitrogen atmosphere. After cooling, filtration, neutralization and evaporation of the volatile parts, the crude residue was distilled under reduced pressure: 0.5-1 Torr. The following table summarizes the obtained results.

| Starting epoxide | Amount (g) | Final product | Amount (g) |
|---|---|---|---|
| (A) | 10 → | (IA) | 9.2 |
| (B) | 10 → | (IB) | 8.7 (≧90%) |
| (A) + (B) + (A') 60:35:5 | 10 → | (IA) + (IB) 65:35 | 9.2 |

The tricyclic alcohols cited in the above table were characterized as follows:

(IA) m.p. 73° (crystallization in petrol ether);
IR (CDCl$_3$): 3400, 3080, 1660, 1050, 890 cm$^{-1}$;
NMR (360 MHz, CDCl$_3$): 1.44 (1H, d); 1.55 (3H, d); 1.76 (1H, d); 2.14 (1H, d); 2.24 (1H, d); 2.28 (1H, m); 2.66 (1H, m); 2.82 (1H, d); 2.87 (1H, m); 3.96 (1H, d); 4.9 (1 H, s); 4.98 (1H, s); 5.14 (1H, m)δppm;
MS: M$^+$=176(12); m/e: 158(1), 143(7), 128(5), 115(4), 105(6), 96(40), 81(100), 67(6), 53(7), 41(10), 27(7).

(IB) m.p. 46° (crystallization in petrol ether);
IR (CDCl$_3$): 3400, 3080, 1780, 1660, 1642, 1400, 1200, 820 cm$^{-1}$;
NMR (360 MHz, CDCL$_3$): 1.44 (1H, d); 1.64 (3H, s); 1.74 (1H, dxt); 2.1 (1H, d); 2.2 (1H, dxd); 2.24 (1H, d); 2.68 (1H, m); 2.75 (1H, d); 3.05 (1H, m); 3.80 (1H, m); 4.85 (1H, s); 4.98 (1H, s); 5.0 (1H, m)δppm;
MS: M$^+$=176(12); m/e: 158(2), 143(8), 128(5), 114(4), 106(7), 96(90), 81(100), 80(60), 79(40), 67(8), 53(9), 41(13), 27(9).

Esters of 3-methyl-9-methylene-endo-tricyclo[5.2.1.0$^{2,6}$]dec-3-en-8(exo)-ol(IA)

(a) formic acid ester

Prepared from 10 g of alcohol (IA) and 100 ml of 98% formic acid (92% yield).
IR: 3080 3045, 1720, 1670, 910, 820, 805 cm$^{-1}$;
NMR: 1.58 (3H, m); 5.0 and 5.2 (2×2H, 2 m); 5.0 (1H, s); 5.2 (1H, m); 8.1 (1H, d, J=2 Hz)δppm;
MS: M$^+$=204(2); m/e: 176(1), 158(80), 143(65), 128(20), 91(20), 81(100), 80(95), 79(70), 53(15).

(b) acetic acid ester

Prepared from 10 g of alcohol (IA), 50 ml of acetic anhydride and 3 drops of concentrated phosphoric acid: reaction temperature 40°-50° (92% yield).
b.p. 120°-140°/0.1 Torr;
IR: 3090, 3045, 1740, 1670, 1650, 905 cm$^{-1}$;
NMR: 1.57 (3H, m); 2.03 (3H, s); 4.9-5.3 (4H, several m)δppm;
MS: M$^+$=218(5); m/e: 176(16), 158(85), 143(82), 128(24), 91(18), 80(100), 79(85), 43(60).

(c) propionic acid ester

Prepared from 1.6 g of alcohol (IA), 16 ml of propionic anhydride and 1 drop of concentrated phosphoric acid: reaction temperature 20° (86% yield).
b.p. 130°-135°/0.1 Torr;
IR: 3090, 3045, 1730, 1675, 1650, 900 cm$^{-1}$;
NMR: 1.17 (3H, t, J=7 Hz); 1.56 (3H, m); 4.9-5.3 (4H, several m)δppm;
MS: M$^+$=232(5); m/e: 176(10), 158(75), 143(80), 129(16), 91(10), 80(100), 79(85), 57(40).

(d) isobutyric acid ester

Prepared from 1.6 g of alcohol (IA), 16 ml of isobutyric anhydride and 1 drop of concentrated phosphoric acid: reaction temperature 20° (87% yield).
IR: 3090, 3045, 1712, 1670, 1645, 905 cm$^{-1}$;
NMR: 1.17 (6H, 2d, J=6 Hz); 1.58 (3H, m); 4.85-5.28 (4H, several m)δppm;
MS: M$^+$=246(5); m/e: 158(70), 143(70), 129(15), 96(20), 80(100), 79(75), 71(48), 43(80).

Esters of 4-methyl-9-methylene-endo-tricyclo[5.2.1.0$^{2,6}$]dec-3-en-8(exo)-ol (IB)

All the esters cited hereinbelow were obtained from alcohol (IB) by following the synthetic method given in Example 2.

(a) formic acid ester

IR: 3090, 3050, 1805, 1720, 1670, 1660, 1180, 905 cm$^{-1}$;
NMR: 1.65 (3H, d, J=1.5 Hz); 4.95 (2H, m); 5.02 (1H, m); 5.10 (1H, m); 8.06 (1H, s)δppm;
MS: M$^+$=204(3); m/e: 176(1), 158(100), 143(60), 128(15), 115(6), 91(16), 81(60), 80(95), 75(85), 65(6), 53(10), 39(15).

(b) acetic acid ester

IR: 3080, 3045, 1800, 1730, 1670, 1660, 1240, 900 cm$^{-1}$;
NMR: 1.70 (3H, m); 2.02 (3H, s); 4.94 (2H, m); 5.0 (1H, m); 5.02 (1H, m)δppm;
MS: M$^+$=218(1); m/e: 176(20), 158(90), 143(90), 128(15), 115(7), 80(100), 79(95), 43(60).

(c) propionic acid ester

IR: 3080, 3045, 1735, 1670, 1650, 1190, 900 cm$^{-1}$;
NMR: 1.13 (3H, t, J=6 Hz); 1.68 (3H, m); 2.32 (2H, q, J=6 Hz); 4.92 (2H, m); 4.95 (1H, m); 5.02 (1H, m)δppm;
MS: M$^+$=232(2); m/e: 176(25), 158(85), 143(90), 129(25), 80(100), 79(94), 57(40), 29(40).

(d) isobutyric acid ester

IR: 3085, 3045, 1730, 1675, 1660, 1180, 1160 cm$^{-1}$;
NMR: 1.15 (6H, 2d, J=7 Hz); 1.67 (3H, m); 4.88 (2H, m); 4.95 (1H, m); 5.0 (1H, m)δppm;
MS: M$^+$=246(3); m/e: 220(1), 176(18), 158(92), 143(90), 80(100), 79(90), 69(50), 55(15), 43(65).

EXAMPLE 2

A base perfume composition destined to be incorporated in shampoos was prepared by mixing the following ingredients (parts by weight):

| | |
|---|---|
| Roman chamomile oil at 5%* | 300 |
| Brazilian rose wood oil | 250 |
| Synthetic geranium oil | 30 |
| Geraniol | 80 |
| Lavandin oil | 30 |
| Linalol | 70 |
| l-Limonene | 70 |
| Dihydrocarvyl acetate at 10%* | 60 |
| Moroccan chamomile oil at 10%* | 60 |
| Synthetic jasmine oil | 50 |
| Ethyl cinnamate | 10 |
| Cinnamyl formate | 10 |
| Caraway oil at 10%* | 50 |

*in diethyl phthalate

The obtained base showed a green aromatic character. By adding to 120 parts thereof 8 parts of 3-methyl-9-methylene-endo-tricyclo[5.2.1.0$^{2,6}$]dec-3-en-8(exo)-yl acetate, there was obtained a novel composition possessing a richer and fresher scent reminiscent of the typical odor of basil leaves.

By substituting the isomeric 4-methyl derivative for the said compound, an analogous effect was observed.

EXAMPLE 3

A Cologne toilet water of "classic" type was prepared by diluting at 3% (by weight) in 85% ethanol the following perfume base composition:

| Ingredients | Parts by weight |
| --- | --- |
| Lemon oil | 250 |
| Bergamot oil | 300 |
| Orange oil | 150 |
| Petitgrain Bigarade | 100 |
| Neroli Bigarade | 20 |
| Lavender oil | 70 |
| White thyme oil | 10 |

By adding to 88 parts by weight of the thus prepared Cologne water 2 parts of 3-methyl-9-methylene-endo-tricyclo[5.2.1.0$^{2,6}$]dec-3-en-8(exo)-yl acetate, the original composition acquired a pleasant green and aromatic fragrance.

By replacing the said acetate by its isomeric 4-methyl derivative, an analogous effect was observed.

While the nomenclature of the novel compounds of this invention follows the IUPAC rules A-31 and A-32, the Chemical Abstracts nomenclature may also be used in regard to the numbering of the ring. Thus, the novel compounds of Example 1 and of claims 3 and 4 which follow may according to the Chemical Abstracts nomenclature read as follows: 4,7-methano-1H-inden-6-ol,3a,4,5,6,7,7a-hexahydro-3-methyl-5-methylene acetate and 4,7-methano-1H-inden-6-ol,3a,4,5,6,7,7a-hexahydro-2-methyl-5-methylene acetate, respectively.

What we claim is:

1. A compound of formula

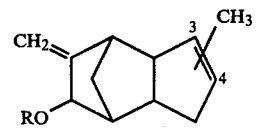

possessing a methyl radical at positions 3 or 4 and wherein symbol R represents a lower acyl radical.

2. A compound according to claim 1, represented by one of the following stereoisomeric forms:

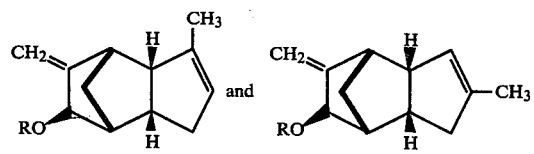

wherein symbol R is defined as indicated in claim 1.

3. 3-Methyl-9-methylene-endo-tricyclo[5.2.1.0$^{2,6}$]-dec-3-en-8(exo)-yl acetate.

4. 4-Methyl-9-methylene-endo-tricyclo[5.2.1.0$^{2,6}$]-dec-3-en-8(exo)-yl acetate.

5. Method for modifying, enhancing or improving the odor properties of perfume compositions or perfumed articles, which comprises adding thereto a small but olfactively effective amount of a compound according to claim 1.

6. A perfume composition which comprises as olfactively active ingredient a compound according to claim 1.

7. A perfumed article, which comprises as olfactively active ingredient a compound according to claim 1.

* * * * *